US00PP26107P2

(12) United States Plant Patent
Johnson, Jr.

(10) Patent No.: US PP26,107 P2
(45) Date of Patent: Nov. 17, 2015

(54) ***BEGONIA* PLANT NAMED 'BASKET CASE PINK'**

(50) Latin Name: ***Begonia* hybrid**
Varietal Denomination: Basket Case Pink

(71) Applicant: Ozzie W. Johnson, Jr., Marietta, GA (US)

(72) Inventor: Ozzie W. Johnson, Jr., Marietta, GA (US)

(73) Assignee: ITSAUL PLANTS LLC, Alpharetta, GA (US)

( * ) Notice: Subject to any disclaimer, the term of this patent is extended or adjusted under 35 U.S.C. 154(b) by 101 days.

(21) Appl. No.: 13/998,171

(22) Filed: Oct. 8, 2013

(51) Int. Cl.
*A01H 5/02* (2006.01)

(52) U.S. Cl.
USPC ..... Plt./343

(58) Field of Classification Search
USPC ..... Plt./343
See application file for complete search history.

*Primary Examiner* — Keith O. Robinson
(74) *Attorney, Agent, or Firm* — Penny J. Aguirre

(57) ABSTRACT

A new cultivar of fibrous *Begonia*, 'Basket Case Pink'., that is characterized by its bronze foliage, its numerous petite soft pink flowers, its plant habit that is compact and mounded with stems trailing as they lengthen, its well-branched stems, its vigorous growth habit, its ability to grow in both sunny and shady conditions, and its ability to produce compact and full containers and be used as a filler plant in combination planters for its trailing stems.

2 Drawing Sheets

Botanical classification: *Begonia* hybrid.
Cultivar designation: 'Basket Case Pink'.

BACKGROUND OF THE INVENTION

The present invention relates to a new and distinct cultivar of *Begonia* plant, botanically of hybrid origin and known as *Begonia* 'Basket Case Pink' and will be referred to hereafter by its cultivar name, 'Basket Case Pink'. 'Basket Case Pink' represents a new fibrous *Begonia* grown for use as a hanging basket and container plant.

The new cultivar was derived from a breeding program conducted by the Inventor in Marietta, Ga. The overall purpose of the breeding program is to make new selections of *Begonia* plants that are floriferous with uniquely colored foliage, good branching and suitable for container production. 'Basket Case Pink' originated as a seedling that arose from seed planted from open pollination of 'Kaylen' (not patented) in Marietta, Ga. in fall of 2009. 'Basket Case Pink' was selected as a single unique plant in 2011 from amongst the resulting seedlings.

Asexual propagation of the new cultivar was first accomplished by stem cuttings in Marietta, Ga. in summer of 2010 by the Inventor. Asexual propagation by stem cuttings, has determined that the characteristics of the new cultivar are stable and are reproduced true to type in successive generations.

SUMMARY OF THE INVENTION

The following traits have been repeatedly observed and represent the characteristics of the new cultivar, which in combination distinguish 'Basket Case Pink' as a new and distinct cultivar of *Begonia*.

1. 'Basket Case Pink' exhibits bronze foliage.
2. 'Basket Case Pink' exhibits numerous petite soft pink flowers.

3. 'Basket Case Pink' exhibits a plant habit that is compact and mounded with stems trailing as they lengthen.
4. 'Basket Case Pink' exhibits a vigorous growth habit.
5. 'Basket Case Pink' exhibits well-branched stems.
6. 'Basket Case Pink' is able to grow well in both sunny and shady conditions (light shade to dappled sun is preferred).
7. 'Basket Case Pink' produces compact and full containers and is well suited as a filler plant in combination planters for its trailing stems.

The female parent of 'Basket Case Pink', 'Kaylen', differs from 'Basket Case Pink' in being taller in height, in having a more upright plant habit, in having leaves that are deeper veined with distinct crenate margins, and in producing tubers. 'Basket Case Pink' can be most closely compared to plants of the *Begonia* Cocktail seed strain 'Gin' (not patented) and typical plants of the species *Begonia solananthera*. 'Gin' is similar to 'Basket Case Pink' in having bronze foliage and pink flowers. 'Gin' differs from 'Basket Case Pink' in being taller in height, in having upright stems (non trailing), in having larger flowers and leaves, and in having lighter colored foliage when grown under light shade conditions. Plants of *Begonia solananthera* are similar to 'Basket Case Pink' in having numerous small flowers and in having trailing stems. Plants of *Begonia solananthera* differ from 'Basket Case Pink' in having green leaves that are cordate in shape, and in having flowers that are white in color with a red eye.

BRIEF DESCRIPTION OF THE DRAWINGS

The accompanying colored photographs illustrate the overall appearance and distinct characteristics of the new *Begonia*. The photographs were taken of a plant about one year in age as grown in a 10-inch container in a greenhouse and cut back several times during production.

The photograph in FIG. 1 provides a side view of 'Basket Case' in bloom.

Figure 1:
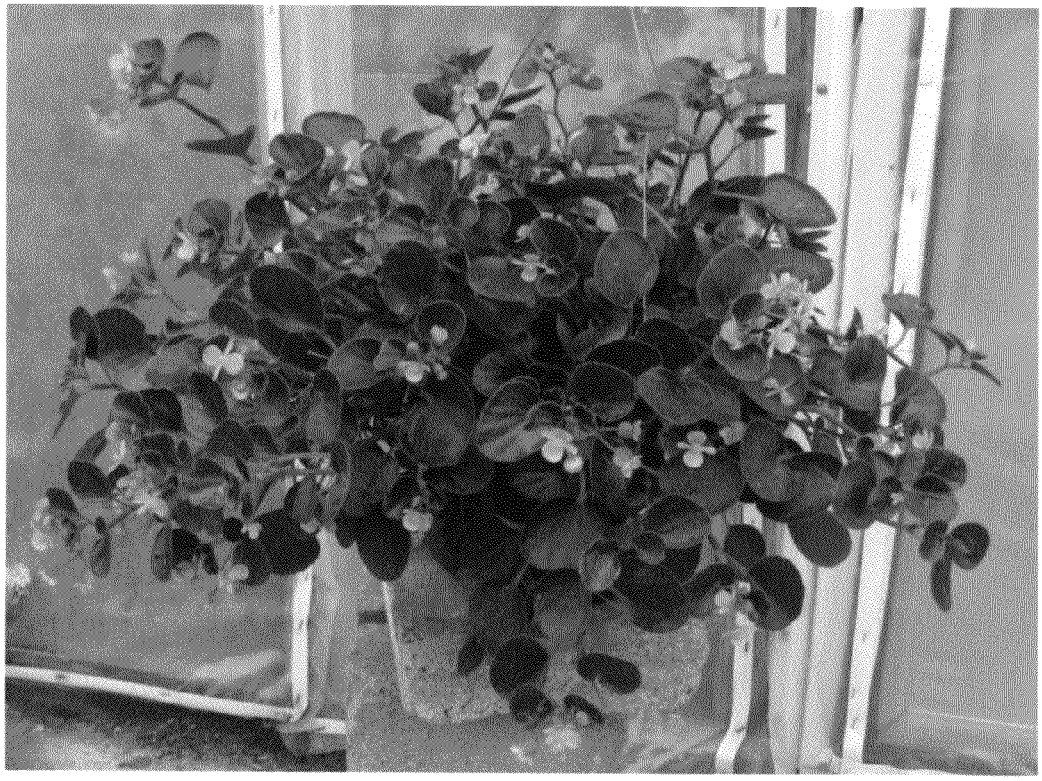
Figure 2:
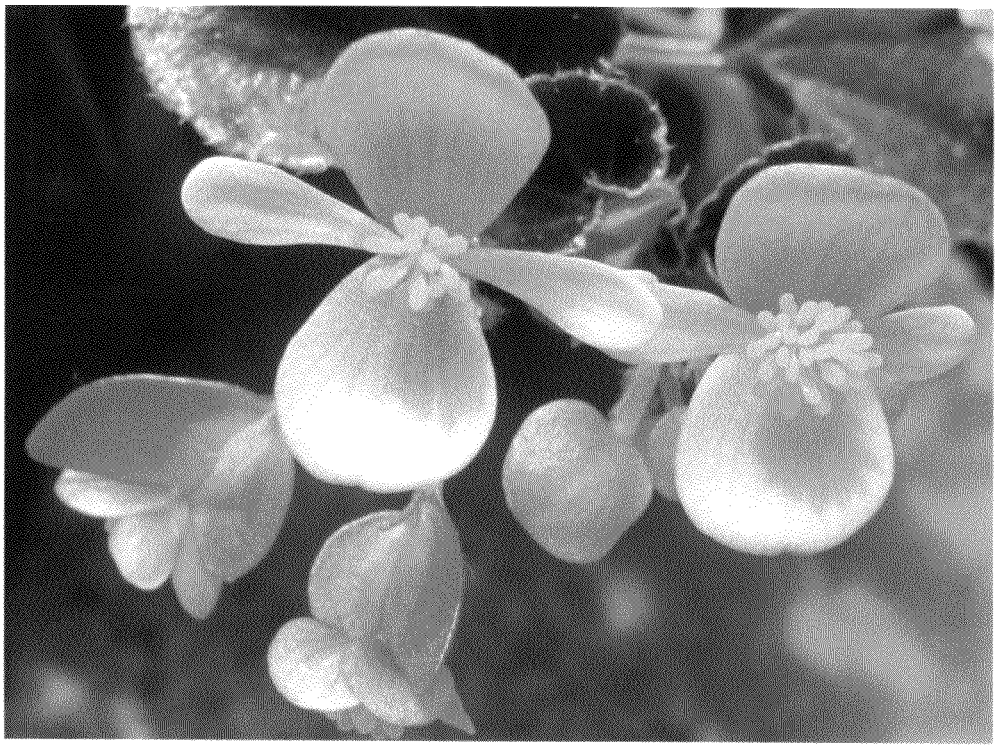

The photograph in FIG. 2 provides a close-up view of the flowers of 'Basket Case'.

The colors in the photographs may differ slightly from the color values cited in the detailed botanical description, which accurately describe the colors of the new *Begonia*.

DETAILED BOTANICAL DESCRIPTION OF THE PLANT

The following is a detailed description of plants of the new cultivar about one year in age as grown in 10-inch containers in a greenhouse and cut back several times during production. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General plant characteristics:

*Plant type*.—Deciduous perennial, grown as an annual for use as a container plant, fibrous type *Begonia*.

*Plant habit*.—Compact and mounded with stems trailing as they lengthen.

*Flowering period*.—Blooms year around under warm greenhouse conditions with fewer flowers during 15 to 25 cm in height and about 50 cm in width, trailing stems can reach up to 45 cm in length.

*Cold hardiness*.—At least to U.S.D.A. Zone 9.

*Culture*.—Grows well in both sunny and shady conditions (light shade to dappled sun is preferred).

*Diseases and pests*.—Has shown resistance to powdery mildew (*Oidium begonia*), no susceptibility to diseases or pests has been observed.

*Root description*.—Fibrous (no tubers produced) and NN155C in color.

*Time required for root development*.—An average of two weeks for root initiation with young rooted plant produced in an average of four weeks.

*Growth rate*.—Vigorous.

*Propagation*.—Stem cuttings.

Stem description:

*Stem size*.—Main stems; an average of 15 cm in length and 4 mm in width with swollen nodes about 7 mm in width, lateral branches; an average of 10 cm in length and 3 mm in width with swollen nodes about 5 mm in width.

*Stem shape*.—Oval, solid, swollen nodes, slightly zigzag.

*Stem color*.—Main and lateral stems; a blend of 183A and 166A.

*Stem surface*.—Main and lateral stems; glabrous in texture and shiny.

*Stem strength*.—Main and lateral stems; moderately strong.

*Internode length*.—Average of 2 cm in main stems and 1 cm in lateral stems.

*Branching habit*.—Well-branched; an average of 20 main stems with an average of 6 lateral stems per main stem (an average of 120 total lateral stems per plant).

*Branching angle*.—Main stems; emerge upright and become pendulant, lateral stems; variable but primarily horizontal and also pendulant with growth.

Foliage description:

*Leaf shape*.—Primarily round.

*Leaf type*.—Simple.

*Leaf division*.—Entire.

*Leaf base*.—Rounded and slightly oblique.

*Leaf apex*.—Round.

*Leaf venation*.—Palmate, not conspicuous, color matched leaf color.

*Leaf margins*.—Appear entire but very slight crenated with very small spines.

*Leaf attachment*.—Petiolate.

*Leaf arrangement*.—Alternate.

*Leaf surface*.—Upper surface; glabrous and glossy with small pits, lower surface; glabrous and satiny.

*Leaf color*.—Upper surface new leaves; a color between N77A and 166A, lower surface new leaves; 183B, upper surface mature leaves; a color between a color between 200A and N189A, lower surface mature leaves; 183B.

*Leaf size*.—Mature up to 4 cm in length and width.

*Leaf fragrance*.—None.

*Petioles*.—Ranges from 0.5 cm to 5 cm in length (average of 3.5) and an average of 2 mm in width, surface is glabrous, color is nearest 176B.

*Stipules*.—Broadly lanceolate in shape, 147C in color and suffused with 176B, rapidly becoming dry and papery, about 7 mm in length and 4 mm in width.

Flower description (male and female flowers):

*Inflorescence type*.—Cymes of single flowers produced in the axils of the upper leaves, monoecious.

*Inflorescence size*.—An average of 3 cm in length and 2.5 cm in width.

*Peduncles*.—About 7 mm in length and 1 mm in width, a blend of 63A and 145D in color, glabrous surface, moderate strength.

*Flower persistence*.—Self-cleaning, flowers last about 5 days.

*Flower type*.—Single.

*Flower fragrance*.—None.

*Flower number*.—Average of 7 flowers per cyme with an average of 1 cyme per lateral stem.

*Flower aspect*.—Upright terminal with lower flowers outward.

*Bracts*.—Typically 2 per cluster, oblong in shape, hairy apex, truncate base, about 3 mm in length and 2 mm in width, 146D in color, margins with stiff hairs.

*Pedicels*.—An average of 5 mm in length and 1 mm in width, a blend of 63A and 145D in color, glabrous surface, moderate strength.

*Flower buds*.—Flattened round-oval in shape, about 5 mm in length and 6 mm in width, 63C in color, glabrous and smooth surface texture.

*Flower shape*.—Campanulate.

*Flower size*.—About 5 mm in length and 7 mm in width.

*Outer tepal*.—2, un-fused, ovate in shape, obtuse apex, rounded to base, average of 5 mm in length and 7 mm in width, glabrous and smooth on outer and inner surface, entire margin, outer and inner surface; a blend of 63B and 63C.

*Inner tepal*.—2, un-fused, oblanceolate in shape, broadly acute apex, attenuate base, average of 5 mm in length and 3 mm in width, glabrous and smooth on inner and outer surface, entire margin, outer surface and inner surface a blend of 63B and 63C in color.

Reproductive organs:

*Stamens*.—About 22, arranged in a cluster, filaments are about 1.5 mm in length and 1B in color, anthers are oblong in shape, basifixed, about 1.5 mm in length and 1 mm in width, 1B in color, pollen is moderate in quantity and 4D in color.

*Pistils*.—1, filament is stout, about 1.5 cm in length and width, and N144B in color, stigmas have 3 branched pairs, are about 1.5 mm in height and width, and N144B in color, ovary is one celled, inferior, about 5 mm in height and 3 mm, and 145D in color with 2 wings (one 2 cm in width and 5 mm in height and one 4 cm in width and 5 mm in height) that are a blend of 63B and 63C in color.

*Fruit and seed*.—Fruit; tri-lobed seed capsule, winged on upper lobe, 8 mm in length, 6 mm in width, rounded on the bottom, the upper wing is 4 mm in height and extends the length of the capsule, color 145D with wings a blend of 63B and 63C in color, stigma are persistent through drying, seed; hundreds, oblong in shape, a fraction of a millimeter in length, color a blend of N199B and N199C.

It is claimed:

1. A new and distinct cultivar of *Begonia* plant named 'Basket Case Pink' as herein illustrated and described.

* * * * *